United States Patent [19]
Dewez et al.

[11] Patent Number: 5,962,136
[45] Date of Patent: Oct. 5, 1999

[54] BIOMATERIAL AND METHOD FOR OBTAINING IT

[75] Inventors: Jean-Luc Dewez, Bousval; Jean-Benoit Lhoest, Louvain-La-Neuve; Eric Detrait, Loverval; Paul Rouxhet, Chastre; Patrick Bertrand, Louvain-La Neuve; Philippe Van Den Bosch De Aguilar, Wavre, all of Belgium

[73] Assignee: Universite Catholique de Louvain, Belgium

[21] Appl. No.: 08/849,067

[22] PCT Filed: Nov. 14, 1995

[86] PCT No.: PCT/BE95/00104

§ 371 Date: Oct. 3, 1997

§ 102(e) Date: Oct. 3, 1997

[87] PCT Pub. No.: WO96/15223

PCT Pub. Date: May 23, 1996

[30] Foreign Application Priority Data

Nov. 14, 1994 [BE] Belgium ............... 09401022

[51] Int. Cl.⁶ ............ G01N 33/543; C12N 5/00; C12N 11/08; C12O 1/00

[52] U.S. Cl. .......... 428/410; 428/423.1; 623/1; 424/422; 424/423; 427/2.24

[58] Field of Search .............. 428/410, 423.1; 623/11, 1; 424/422, 423; 427/2.24

[56] References Cited

U.S. PATENT DOCUMENTS

| | | | |
|---|---|---|---|
| 5,055,316 | 10/1991 | Hoffman et al. | 427/2 |
| 5,308,704 | 5/1994 | Suzuki et al. | 428/410 |
| 5,607,475 | 3/1997 | Cahalan et al. | 623/4 |

*Primary Examiner*—Nathan M. Nutter
*Attorney, Agent, or Firm*—Knobbe Martens Olson & Bear, LLP

[57] ABSTRACT

The present invention concerns a biomaterial for the selective adhesion of cell and/or tissue, which comprises a polymeric support having an heterogeneous surface conditioned with a surfactant and an extracellular matrix protein or a portion of said protein. The present invention concerns also the biosensor, the diagnostic device, the bioreactor, the tissue and the organ comprising the biomaterial according to the invention.

22 Claims, 15 Drawing Sheets

BIOMATERIAL AND METHOD FOR OBTAINING IT

CONTINUING DATA

This application is filed under 35 USC 371 of PCT/BE95/00104, filed Nov. 14, 1995.

FIELD OF THE INVENTION

The present invention is related to a new biomaterial for the selective adhesion of cells or tissues.

The present invention is also related to the biosensor, the bioreactor, the diagnostic device, the tissue and/or the organ comprising said biomaterial.

The present invention is also related to the method for obtaining said biomaterial.

BACKGROUND OF THE INVENTION AND STATE OF THE ART

The polymeric structures are widely used as a solid support in the medical and biochemical fields.

For organs such as skin, mucosa, blood vessels, liver and spleen the functions of which cannot be replaced satisfactorily with artificial material alone, the trend to develop hybrid artificial organs of integrated cell type has been more popular in recent years.

In such case, an important issue resides in the selection and design of matrix materials on which cells are cultured. For example, it is well known that the adhesion, growth and proliferation of endothelial cells depend on the solid support offered to the cells.

Matrices are generally constituted of polymer materials and such polymer materials have conventionally been surface modified by a variety of processes.

Surface modification processes are schematically grouped in dry processes, representatively illustrated by plasma processes, arc processes, etc., and wet processes represented by coating, graft polymerization, etc.

The plasma processes include for example non reactive plasma processes based on the sputtering action of inactive ions such as argon, reactive plasma processes using active gas such as oxygen.

The surface matrix obtained by said plasma processes is homogeneously modified.

The coating is conducted by precoating an adhesive protein in solution from connective tissues such as collagen, fibronectin, etc. onto a matrix surface, thereby iiproving the adhesion of cells (endothelial cells, fibroblasts, etc.)

The documents J63196283 and J07108060 describe materials comprising a polymer (previously treated with U.V., electron beam or ion irradiation), coated with sugars, proteins or lipids. Said materials are used in culture of animal cells and for the diagnostic of cancer.

However, for the development of new biomaterials, it becomes important to produce heterogeneous surfaces with path such that preferential cell adhesion can occur. By such strategy it will be possible to guide the cell growth along preferential directions for specific applications such as nerve reconstruction.

In addition, for in vivo studies, it is better to obtain biomaterials whose chemical composition is closer to biological materials (biomaterials containing only carbon, hydrogen, oxygen and nitrogen).

AIMS OF THE INVENTION

The present invention aims to provide a new biomaterial for the selective adhesion of cells and/or tissues which do not present the drawbacks of the state of the art.

A main aim of the invention is to obtain a biomaterial allowing preferential cell and/or tissue adhesion in order to guide the cell and the tissue growth along preferential directions, particularly for specific applications such as nerve reconstruction.

Another aim of the invention is to obtain a biomaterial which is biocompatible.

Another aim of the invention is to obtain a biomaterial which may be used for the diagnostic of cancer.

A further aim of the invention is to provide an improved biosensor, bioreactor, diagnostic device, organ and/or tissue comprising the biomaterial according to the invention.

A last aim of the invention is to provide a method to obtain the biomaterial according to the invention which is reproducible and may be easily used on a industrial scale.

SUMMARY OF THE INVENTION

The present invention concerns a biomaterial for the selective adhesion of cell and/or tissue, which comprises a polymeric support having an heterogeneous surface conditioned with an extracellular matrix protein (or a portion thereof) and a surfactant.

A polymeric support having an heterogeneous surface means a polymeric support having surface modified areas and non-modified surface areas (or unmodified surface areas). Preferably, said surface modified areas show a different hydrophobicity compared to the non modified surface areas.

It seems that the protein (or a portion thereof) of the extracellular matrix segregates only upon specific surface areas (preferably the modified surface areas) of the polymeric support. On the other side, it seems that the surfactant adsorption is observed mostly upon the other surface areas, where it inhibits the adsorption of the extracellular matrix protein or a portion thereof.

Therefore, it seems that when the heterogeneous surface of a polymeric support is conditioned with an extracellular matrix protein (or a portion thereof) and a surfactant according to the invention, the biomaterial obtained reveals at its surface a large difference of chemical composition between the modified and the non modified areas.

The Inventors have also discovered that a preferential cell adhesion is confined upon said extracellular matrix protein (or a portion thereof) and that there is a good spreading and confluence of these cells upon said surface areas of the polymeric support.

Therefore, the term "surfactant" means any surface active compound which may inhibit the adsorption of an extracellular matrix protein (or a portion thereof) upon specific surface areas, preferably the non modified surface areas of the polymeric support.

According to the invention, the polymeric support having the heterogeneous surface is thus conditioned with a solution which comprises said extracellular matrix protein (or a portion thereof) and the surfactant.

The terms "conditioned with" mean that the polymeric support is covered (or coated) with said surfactant and protein (for instance by the addition of a solution comprising these both products, the solvent being thereafter evaporated).

Extracellular matrix proteins are preferably chosen among the group consisting of collagen, laminin, fibronectin, fibrin, chondronectin or a mixture thereof.

The terms "a portion of an extracellular matrix protein" mean any fragment of said protein (or epitope) (polypeptide, peptidomimetic molecule, . . . ) which may bind one or more antibodies directed against said protein.

Said portion may bind in vitro one or more antibodies directed against the extracellular matrix protein described above, and said binding can be detected in vitro by the methods well known by the Man Skilled in the Art.

Advantageously, the surfactant according to the invention is selected from the group consisting of fatty acids (such as caprylic, behenic, oleic, arachidonic acids, . . . ), their esters, their amides, proteins (such as albumin, etc.), saccharides, lipids, alkyl and aryl sulfates, sulfonates, alcohols, amines, ethers or a mixture thereof.

Advantageously, the surfactant is a non-ionic surfactant such as a triblock copolymer, preferably a polyethylene oxide-polypropylene oxide-polyethylene oxide, such as the $PEO_{70}$-$PPO_{30}$-$PEO_{70}$ (pluronic-F68®).

According to the invention, the polymeric support is selected from the group consisting of the olefin polymers, the fluorin polymers, the polystyrene, the polyacrylic polymers, the polyesters polymers, the polyurethane polymers, the silicon polymers, the cellulose polymers, the epoxy polymers or a mixture thereof.

Preferably, said polymeric support is made only of carbon, hydrogen, oxygen and/or nitrogen.

The present invention concerns also the biosensor, the bioreactor, the diagnostic device (such as a diagnostic kit or a chromatographic column), the tissue and/or the organ comprising the biomaterial according to the invention (for instance, as a solid support of said product).

Said tissue and organ are natural or artificial, vegetal or animal, tissue and organ.

Another aspect of the present invention is related to the method for obtaining the biomaterial according to the invention wherein the surface of a polymeric support is treated by an ion beam and thereafter, conditioned with a surfactant and a protein (or a portion thereof) of the extracellular matrix.

Advantageously, said ion beam is a $He^+$ beam, a $Xe^+$ beam and/or a $Ga^+$ beam.

Preferably, the fluence of the ion beam is comprised between $10^{10}$ and $10^{20}$, preferably between $10^{12}$ and $10^{16}$ ions/cm$^2$ of polymeric support surface.

The present invention also concerns the method for obtaining the biomaterial according to the invention wherein the surface of a polymeric support is partially covered by a mask, wherein the surface of the polymeric support is treated by a plasma discharge, preferably a $O_2$ plasma discharge, wherein the mask is removed and wherein the polymeric support is conditioned with a surfactant and a protein (or a portion thereof) of the extracellular matrix.

Advantageously, the surface of the polymeric support is treated by the plasma discharge between 10 sec and 60 sec at a power of comprised between 10 and 100 Watts, preferably around 50 Watts.

The last aspect of the present invention concerns the use of the biomaterial according to the invention for the cell and/or tissue culture. These cells are preferably animal cells such as human cells (hybridoma cells, diploid fibroblasts strain LRC-90 from human lung, cells V-79 derived from the lung of Chinese hamster, HeLa cells, MRC5 cells from the lung of human embryo, vascular endothelial cells, neuronal cells, hepatocytes, blood cells, . . . ) which may be used for the production of drugs, vaccines, hormones, interferons, cytokines, . . . .

The biomaterial according to the invention may also be used for the screening of cells, and particularly for the diagnostic of tumour cells, as the cancerous cells may adhere differently than the normal cells on specific areas of the biomaterial according to the invention.

In the following examples, the Inventors demonstrate that a polymeric support having an heterogeneous surface presents an hydrophobicity contrast between different areas large enough to induce a more irreversible surfactant adsorption in the most hydrophobic areas, leading to a protein selective adsorption in the most hydrophilic ones. Therefore, it seems that the cells adhesion, spreading and proliferation occur only upon said areas where proteins were present.

The present invention will be further described in the examples in view of the following drawings.

BRIEF DESCRIPTION OF THE DRAWINGS

Scale bar represents 200 μm.

Bombardment conditions:
a) $4\ 10^{14}\ He^+$ (1 MeV)/cm$^2$ (250× magnification),
b) $5\ 10^{15}\ Xe^+$ (4 keV)/cm$^2$ (125× magnification).

Figure 15:
Figure 16:

FIGS. 15 and 16 represent cells cultivated on the biomaterial according to the invention.

EXAMPLE 1

Materials and Methods

1. Materials

The polystyrene (PS 05232) was purchased from BP.

The photosensitive resin is a novolac type resin (HPR504 from OCG Microelectronic Materials) which contains two main components; a cresol formaldehyde polymer and a photosensitive molecule [2]. The latter contains Naphtoquinone Diazide groups covalently bonded to an unspecified radical by the intermediate of a $SO_3$ group. The Diazide group is removed under irradiation leading to a carboxyl group incorporation. This molecule when modified under U.V., is soluble in the developer while the unmodified one is not. The developer (Waycoat Positive LSI Developer from OCG Microelectronic Materials), used to remove the irradiated resin, contains mainly $Na_2SiO_4$ and $Na_3PO_4$ salts. Unless stated otherwise, the mask used contains 50 µm thick parallel slits allowing the U.V. to pass through, separated by alternately 130 µm and 150 µm thick strips.

The proteins used were rat skin type I Collagen from Boehringer Mannheim and bovine plasma Fibronectin from Sigma. The surfactant was Pluronic F68 from sigma which is a triblock copolymer made of Polyethylene oxide-Polypropylene oxide-Polyethylene oxide ($PEO_{70}$-$PPO_{30}$-$PEO_{70}$). The buffer used was a phosphate buffered saline (PBS) solution (NaCl 137 mM, KCl 2.7 mM, $Na_2HPO_4$ 8 mM, $NaH_2PO_4$ 1.5 mM).

PC12 cell line (rat adrenal pheochromocytoma) [3] were used (ECACC number 88022401). The culture media were a DMEM solution from GIBCO for the serum free medium and the same DMEM solution (4.5 g/l of glucose), 10% horse serum and 5% fetal calf serum were added for the serum containing medium.

The following other products are obtained from:
Ethanol: purity >99% from Merck.
Water: HPLC grade form a milli-Q system from Millipore.
Isopropanol: purity >99% from UCB.

2. Substrate Preparation

The pellets were compression moulded (Pressure of 1.6 MPa) as received at 230° C. between two Kapton sheets giving a 0.2 mm thick film. The PS plates were then cut in 5 cm diameter samples and rinsed in isopropanol under low ultrasonic agitation for 30 min. For the conditioning and cell adhesion experiments, the samples were further cut again in 1.4 cm diameter circles (well diameter) (FIG. 1a)

3. Spin Coating of the Resin and Development

For samples treated on only one face, the resin was spin coated (velocity of 5600 rpm and acceleration of 2000 rpm/sec) on the PS substrate during 30 sec (FIG. 1b) leading to a uniform resin film with a thickness of around 1 µm. After 30 minutes prebake at 95° C., the resin was submitted through a mask to a U.V. light irradiation (1 of 330 nm) for 30 sec (FIG. 1c). The samples were then immersed in a solution containing the developer (50%) dissolved in water (50%) for 90 sec and then rinsed in water for 90 sec. The resin directly irradiated by U.V. light was dissolved in this developer leading to a surface only partially covered with resin (FIG. 1d). For the samples treated on both faces (DCA experiments), after a 5 min. prebake for the first resin coated face, the second face was also spin-coated and a further 30 min. prebake was applied. The samples were then submitted to U.V. light for 90 s. All the other parameters were not modified.

4. Plasma $O_2$ Discharge

Low pressure RF plasma discharge was performed in a barrel reactor (Chemprep 130) with capacitive coupling (13.56 MHz) from Chemex. The reactor chamber was evacuated up to a pressure $\leq 6\ 10^{-5}$ Bar prior to oxygen admission. The discharges were done during 30 sec at a power of 50 Watts and under an oxygen (>99.9999% pure form Air Liquid) flow leading to a working pressure of 6–8 $10^{-4}$ Bar. After the discharge the samples were stored in petry dishes (FIG. 1e).

5. Dissolution of the Remaining Resin

The resin remaining after plasma treatment was dissolved by washing in ethanol for 90 sec and then in water during 90 sec (FIG. 1f).

6. Conditioning

The samples were conditioned in a PBS solution containing 150 µg/ml pluronic and 33 µg/ml protein. The samples were conditioned during 3 hours at 37° C. under saturated water atmosphere and then rinsed three times in PBS prior to other manipulations.

7. Cell Cultures

PC12 were inoculated on the samples in serum free and serum containing culture media in multiwell (24) tissue culture plate from Falcon. Three samples were inoculated for each different treatment. The cellular density was of 100000 or 200000 cells/well (FIG. 1h).

8. Protein and Pluronic Reference Samples for ToF SIMS Analyses

Those samples were obtained by deposition of water solutions (30 µg/ml of fibronectin or 0.01 mg/ml of pluronic) on silicon wafers prior to air evaporation.

Figure 1:
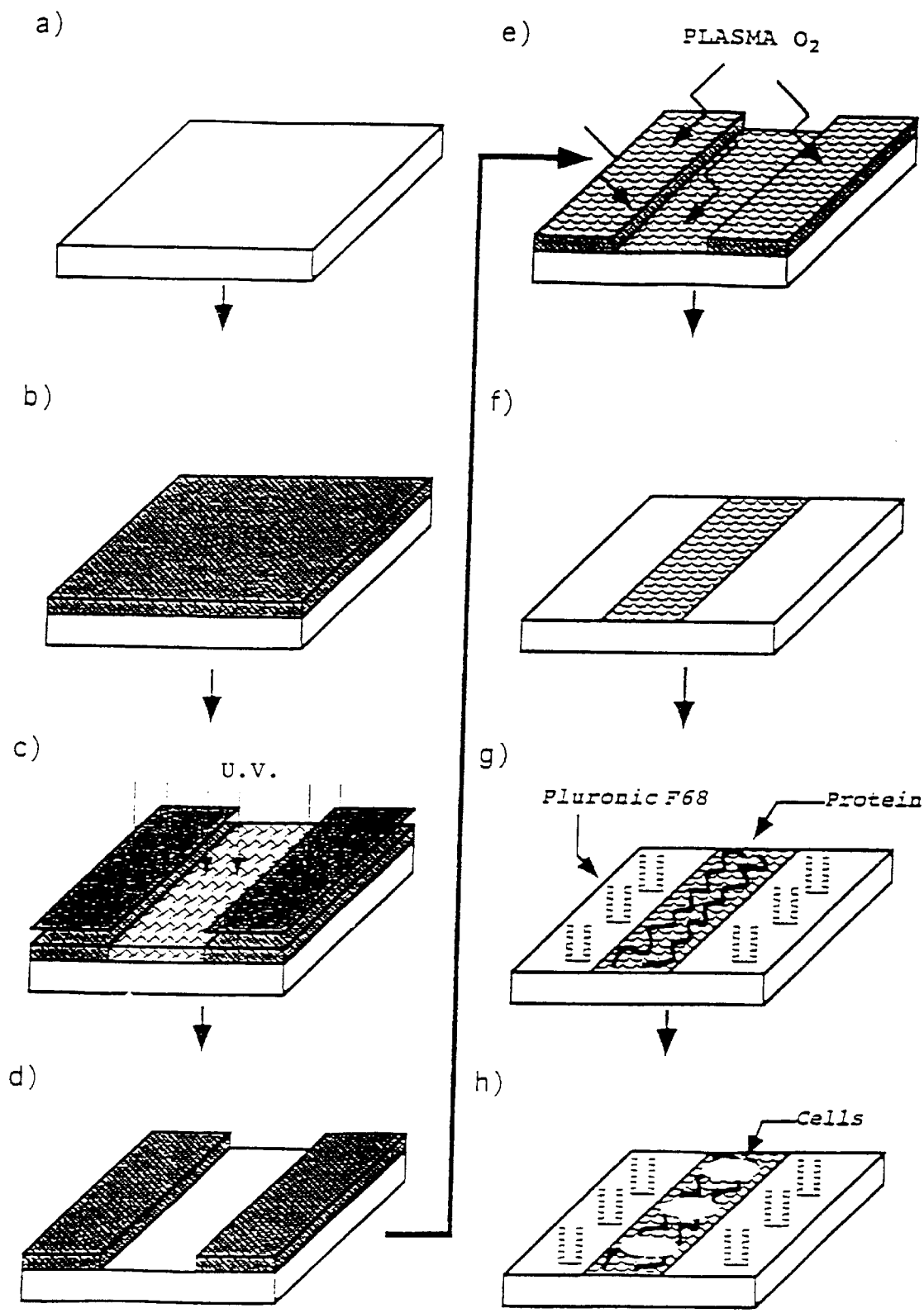
FIGS. 1a through 1h represent schematically the steps followed to obtain the biomaterial of the invention according to a first preparation method.

The different steps of the experimental procedure are illustrated in FIG. 1. This will be used as a guideline throughout the paper.

Figure 2:
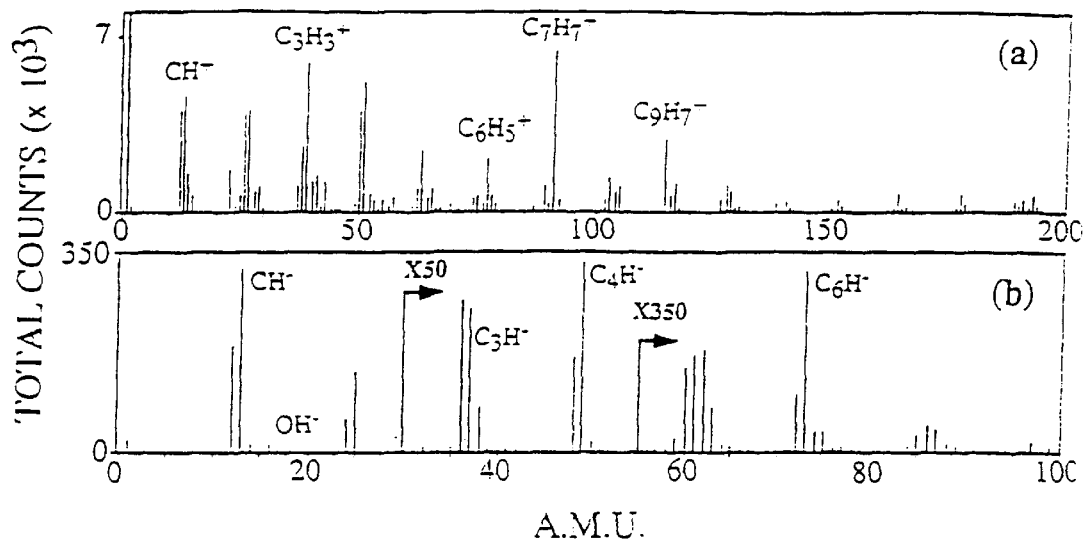
FIGS. 2a and 2b represent typical positive and negative ToF SIMS spectra obtained for a pristine polystyrene sample.

In order to characterize the substrate, Time of flight secondary ion mass spectrometry (ToF SIMS) measurements (Schueler and al., Vacuum 41, p. 1661 (1990) and Microsc. Microanal. Microstruct. 3, p. 119 (1992)) as well as X-ray photoelectron spectroscopy (XPS) (Weng and al., Surf. Interface Analysis 20, p. 193 (1993)) were performed on the pristine polystyrene (PS) samples (FIG. 1a). The positive and negative ToF SIMS spectra of PS are shown in FIG. 2a and 2b respectively. The main contributions to the positive spectrum are coming from unsaturated (small hydrogen content) hydrocarbon peaks. Among those, peaks at 77 ($C_6H_5^+$) and 91 ($C_7H_7^+$) a.m.u. correspond to aromatic ions and are highly characteristic of the presence of the styrene ring. Remark also the $Na^+$ peak at 23 a.m.u. which is a contamination often detected due to the high SIMS sensitivity to this ion. The negative spectrum also contains hydrocarbon peaks characteristics of the PS except for the small oxygen contribution at 16 ($O^-$) and 17 ($OH^-$) a.m.u. This contribution is probably due to a small oxidation during press moulding of the polymer. Note also that no traces of high mass molecular ions characteristic of the presence of additives in the polymer were detected. The XPS results (see Table 1(L1)) confirms the presence of oxygen but the amount detected is very small (1.3%) for a press moulded polymer.

A photosensitive resin commonly used in microelectronic was then spin-coated on the PS substrate and submitted to U.V. irradiation through a mask (FIGS. 1b and 1c). The irradiated resin was further developed in a developer solution (FIG. 1d).

By XPS, the presence of the resin and developer were followed by the S2p and Si2p contributions characteristic of the naphtoquinone molecule and developer respectively. These contributions were detected on undeveloped resin covered samples (Table 1(L2)). In the same time, the presence of the cresol polymer was followed by ToF SIMS. In fact, even if an extensive study is difficult due to the multicomponent resin and developer compositions, cresol formaldehyde characteristic peaks were identified (positive peaks at 121 and 242 a.m.u. and negative peaks at 107 and 227 a.m.u.). Those peaks were attributed respectively to $C_8H_9O^+$ (cresol monomer), $C_{16}H_{18}O_2^+$ (dimer), $C_7H_7O^-$ and $C_{15}H_{13}O^-$.

After the development of the irradiated resin, the samples were submitted to an oxygen plasma discharge and then washed in ethanol and water (FIGS. 1e and 1f) in order to remove the unirradiated resin.

To understand the influence of the plasma treatment and ethanol/water washing, plasma treated pristine PS samples with and without washing were first characterized. XPS results recorded on those samples are also presented in table 1(L3;L4). An $O_2$ Plasma discharge on PS substrates leads to a large oxygen incorporation as shown in table 1(L3) together with a loss of aromaticity [4]. Note also the significant nitrogen contribution. After ethanol/water washing of the surface, the oxygen contribution decreases significantly. This phenomena is attributed to the dissolution of small molecules which often adsorbs on plasma treated surfaces [5]. Positive and negative ToF SIMS spectra recorded on those samples (not shown) revealed also the oxygen incorporation (mainly $O^-$ and $OH^-$ peaks) together with a nitrogen contamination by means of nitrogen containing peaks (mainly $NH_4^+$, $C_5NH_{12}^+$ at 18 and 86 a.m.u. respectively). This last peak is characteristic of highly saturated hydrocarbon chain molecules containing nitrogen atoms. This contamination might come either from contact with air, molecules adsorbed on the barrel walls, or even from additives present in the PS. In fact it is known that under plasma activation, the additives might migrate to the surface of the polymer [6]. Those peaks were more significant before ethanol/water washing than after confirming the low molecular weight molecules dissolution observed by XPS.

For samples partially covered with resin, both areas (resin developed and undeveloped under U.V.) will be presented separately, only after plasma treatment and ethanol/water washing. In the areas were the resin was developed, the PS substrates was supposed to be directly submitted to the active species of the plasma. The oxygen incorporation by the PS is quite similar (Table 1 (L4)) to the one obtained on the same samples without resin. It can also be seen that the S2p and Si2p contributions do not disappear completely but are weak compared to the same value obtained from the pure resin (S2p around 1% of the total intensity). The nitrogen contribution due to the plasma discharge is still significant.

Figure 3:
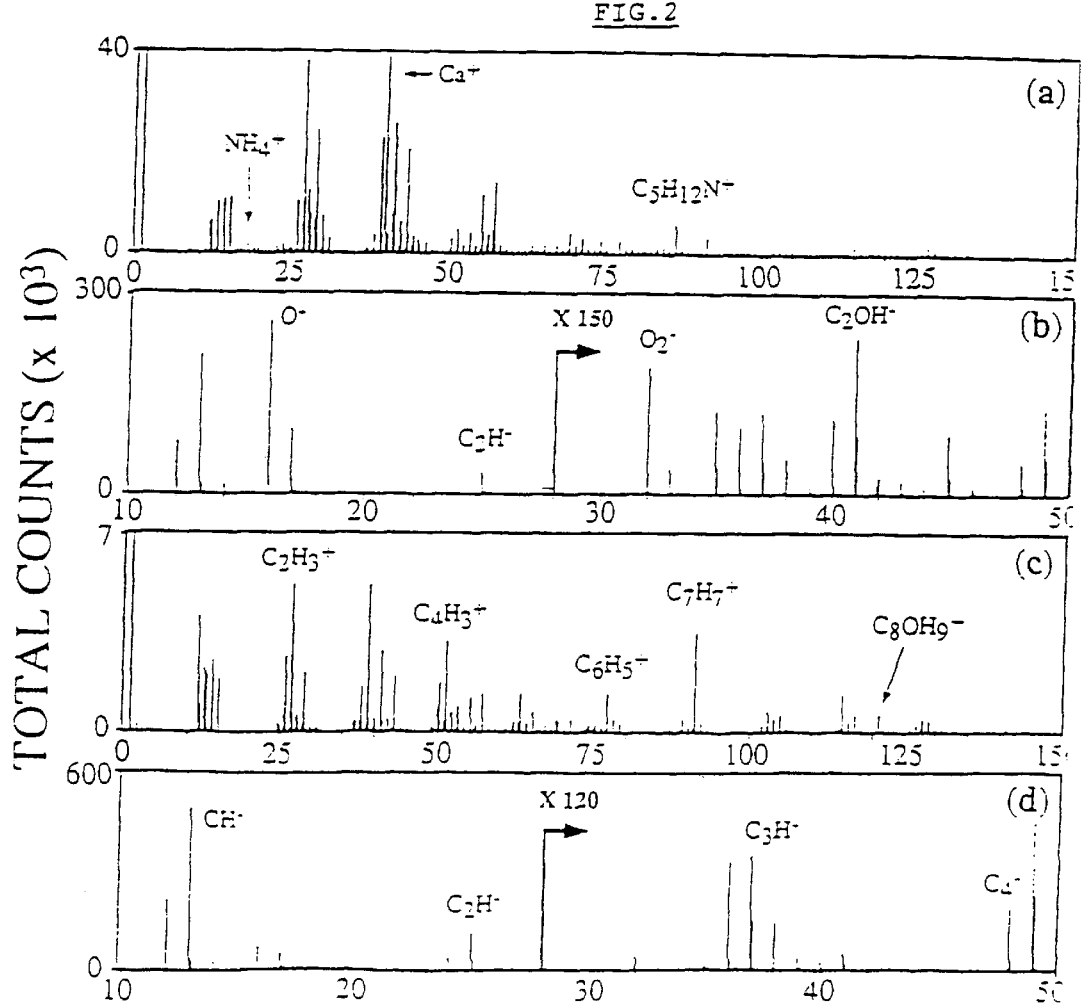
FIGS. 3a through 3d represent:
a) a typical positive ToF SIMS spectrum recorded in resin developed area after plasma treatment and ethanol/water washing;
b) a typical negative ToF SIMS spectrum recorded in resin developed area after plasma treatment and ethanol/water washing;
c) a typical positive ToF SIMS spectrum recorded in resin undeveloped area after plasma treatment and ethanol/water washing;
d) a typical negative ToF SIMS spectrum recorded in resin undeveloped area after plasma treatment and ethanol/water washing.

Positive and negative ToF SIMS spectra recorded on those areas (Plasma treated regions) are also presented in FIGS. 3a and 3b. Those results confirmed the large oxygen incorporation ($O^-$ peak in the negative spectra) and give more information on the induced modifications. Indeed, the cresol peaks (121 a.m.u. and others) from the resin are no more detected after the development and plasma treatment due to degradation under plasma discharge. The $Ca^+$ peak is attributed to a contamination occurring during the water washing. Note also the two nitrogen containing peaks ($NH_4^+$, $C_5NH_{12}^+$) due to the plasma treatment (see supra) which could explain the nitrogen contribution detected by XPS.

From this we suspect the resin components to be, if still present, highly degraded under plasma so that for our purpose, the result is close to what we observed on plasma treated samples without resin.

Within the areas where the resin was not developed, it is expected that the PS substrate was not reached by the plasma active species. In those areas, the amount of oxygen detected (4.5%) was superior to what was obtained on pristine PS (Table 1 (L1 and L5)). This oxygen could be due either to adsorbed ethanol or to the presence of residual resin. No S2p and Si2p contributions were detected by XPS on this part of the sample suggesting a complete removal of the developer and diazoquinone molecules. Positive and negative ToF SIMS spectra (FIGS. 3c and 3d) were seen to be similar to those obtained on pristine PS (FIG. 2) indicating that the PS substrate was not altered by the use of resin as mask for plasma discharge. The main differences are the presence of a small cresol formaldehyde peaks ($C_8OH_9^+$) in the positive spectrum together with more intense oxygen contributions in the negative spectrum, especially for the peak at 41 a.m.u. attributed to $C_2OH^-$ which is probably due to the adsorbed ethanol. The presence of undamaged cresol polymer is an important result since it allows us to conclude that the plasma active species have not significantly reached the PS substrate. Indeed, in that case, the resin peaks should have disappeared like in the developed areas. However, the intensity of this peak is relatively small indicating a strong removal of the cresol polymer. From this we can reasonably assume that the increase of oxygen content in this area is mainly due to adsorbed ethanol and that the use of the resin did not affect significantly the substrate in the undeveloped areas.

Those results suggest the nearly complete removal of the resin on both areas, a small ethanol adsorption in the undeveloped areas as well as the apparition of a nitrogen contamination linked to the plasma treatment in the developed areas.

Figure 4:
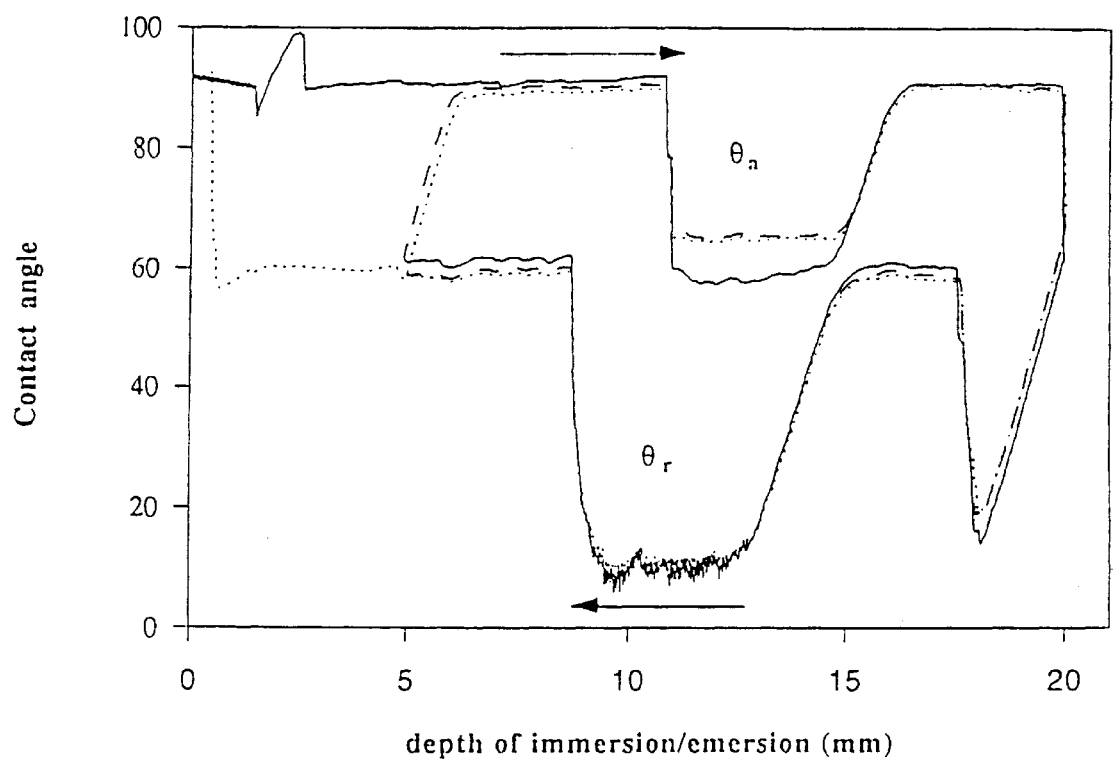
FIG. 4 represents a DCA plot obtained from a partial modified polystyrene surface after plasma treatment and ethanol/water washing.

At this point, a large hydrophobicity step was suspected to occur between the developed and undeveloped areas. This was checked by using DCA. The DCA results obtained on pristine PS gave a $\theta_a$ (advancing angle) and a $\theta_r$ (receding angle) both hydrophobic as expected (see in Table 2). The DCA plot obtained for a sample on which a 5 mm thick tracks resin was developed prior to the plasma discharge and ethanol/water rinsing, is shown in FIG. 4. The contact angle values obtained in the different areas are given in table 2.

As expected, a large hydrophobicity difference was observed between the modified and unmodified areas. The $\theta_a$ observed in the unmodified area was lower but close to the one observed on pristine PS. This is probably linked to the small oxygen incorporation detected by XPS and ToF SIMS. In the modified area, $\theta_a$ is smaller (30°) due to the oxygen incorporation under plasma discharge. The observed increase between the first and following immersion-emersion cycles in the hydrophilic tracks might be explained by dissolution of small molecular weight molecules and/or surface rearrangements. In our case if dissolution (as seen by XPS) can not be excluded, it can also not be significant since the sample was already rinsed in ethanol and water before DCA measurement. The receding angles followed the same evolution with an even more important hydrophobicity difference between the different areas. However, the exact receding angles values are much more sensitive to experimental limitations than advancing ones. Indeed, if an error is made, for example, in the perimeter estimation, the force calculated by DCA varying as $\cos(\theta)$, the error will be more important for smaller contact angles.

Figure 5A:
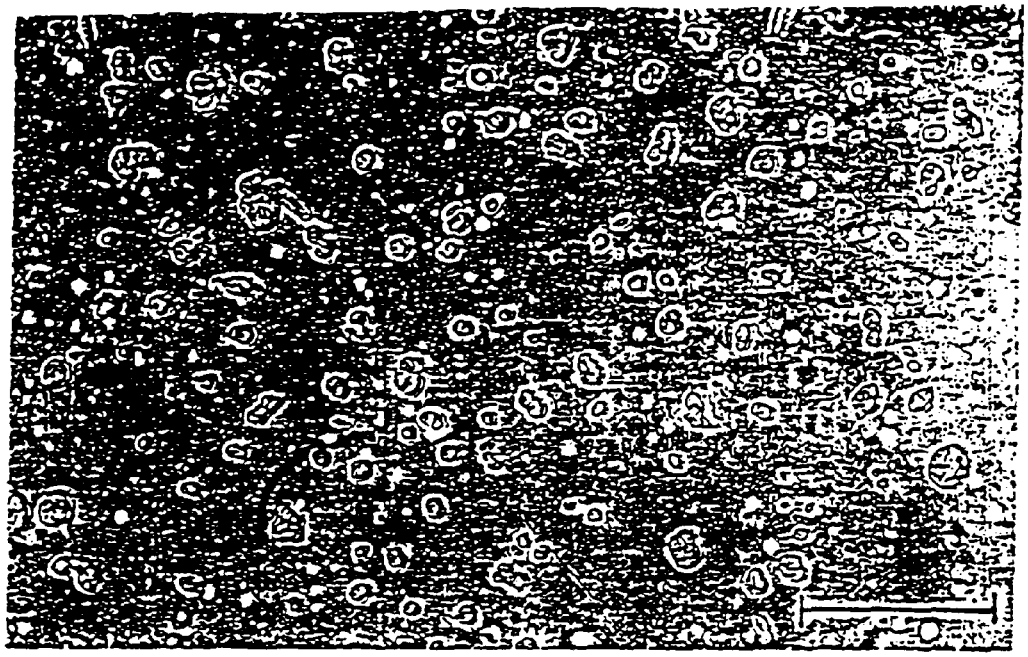
FIGS. 5a through 5c represent:
a) cell culture results on non-conditioned heterogeneous surfaces 24 hours after inoculation at 200000 cells/well in a serum free culture medium;
b) cell culture results on non-conditioned heterogeneous surfaces 3 days after inoculation at 200000 cells/well in a serum containing culture medium;
c) cell culture results on conditioned heterogeneous surfaces 3 days after inoculation at 100000 cells/well in a serum containing culture medium. Scale bar represents 200 μm.
Figure 5B:
Figure 5C:
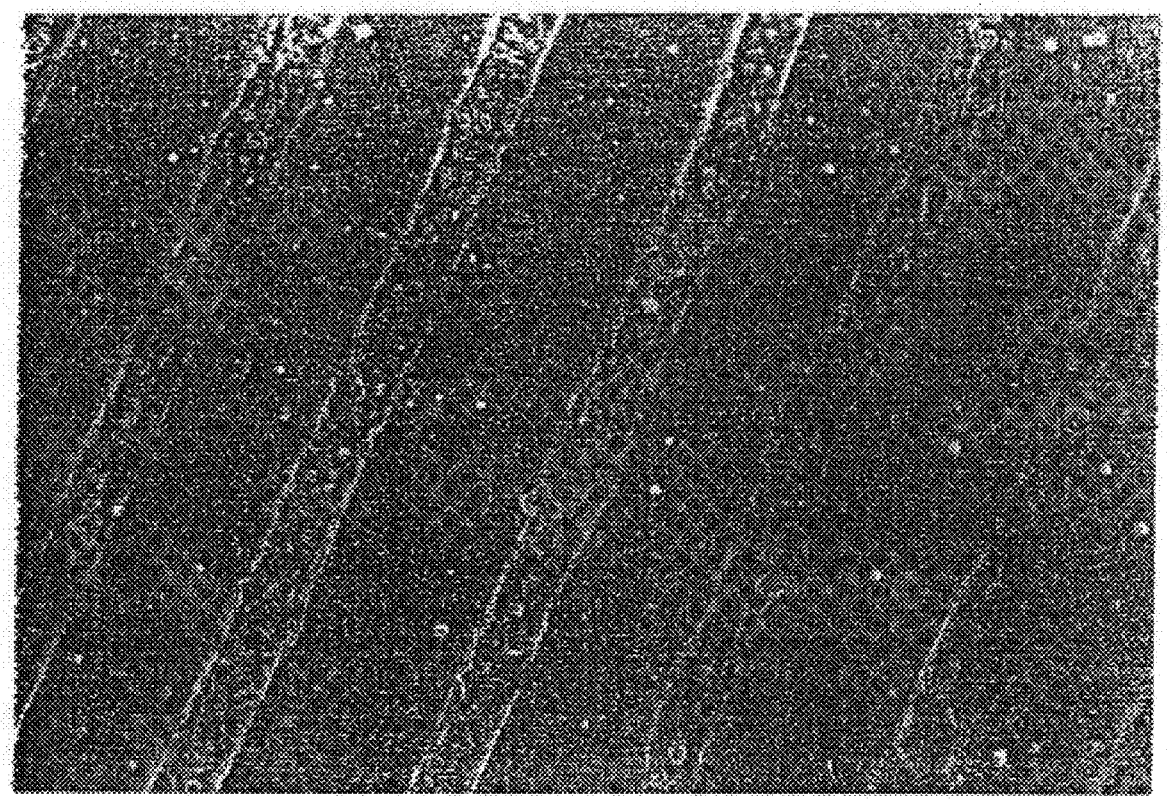

The DCA measurements confirm that an heterogeneous surface is obtained which contains hydrophilic regions surrounded by more hydrophobic ones. Adhesion tests with PC12 cells performed on those samples are presented in FIGS. 5a and 5b for serum free and serum containing media respectively. When serum free culture medium is used (FIG. 5a) no preferential cell adhesion was observed, as suspected [3], and the cell shape was predominantly globular. This means that the PC12 cell adhesion is not affected by such hydrophobicity differences and let us suppose that those cells need specific proteins to adhere on. For serum containing medium, the contrast is better and the cells are well spread, probably due to the presence of some of those specific proteins present in the culture medium. It is not possible to conclude from this picture if this is simply due to a preferential protein adsorption in the hydrophilic tracks. However, even with serum, some cells remained on the more hydrophobic tracks. In order to reduce their number, the samples were further conditioned with a solution containing both a surfactant (pluronic F68) and a protein (FIG. 1g). Indeed it has been shown that the pluronic adsorbs on the hydrophobic surfaces inhibiting protein adsorption and cell adhesion [1, 7, 8]. Two different kinds of proteins were tested (Collagen I and Fibronectin). Cell cultures were also performed on those samples (FIG. 1h). We expected to obtain a protein segregation in the hydrophilic tracks and a cell adhesion only on the proteins. Serum containing medium was used and the results obtain after three days incubation with fibronectin as protein are presented in FIG. 5c. The cells were confined in the hydrophilic tracks, well spread and at confluence. Remark that a further reconditioning of the hydrophilic tracks by other proteins present in the medium might also have occurred.

Figure 6:
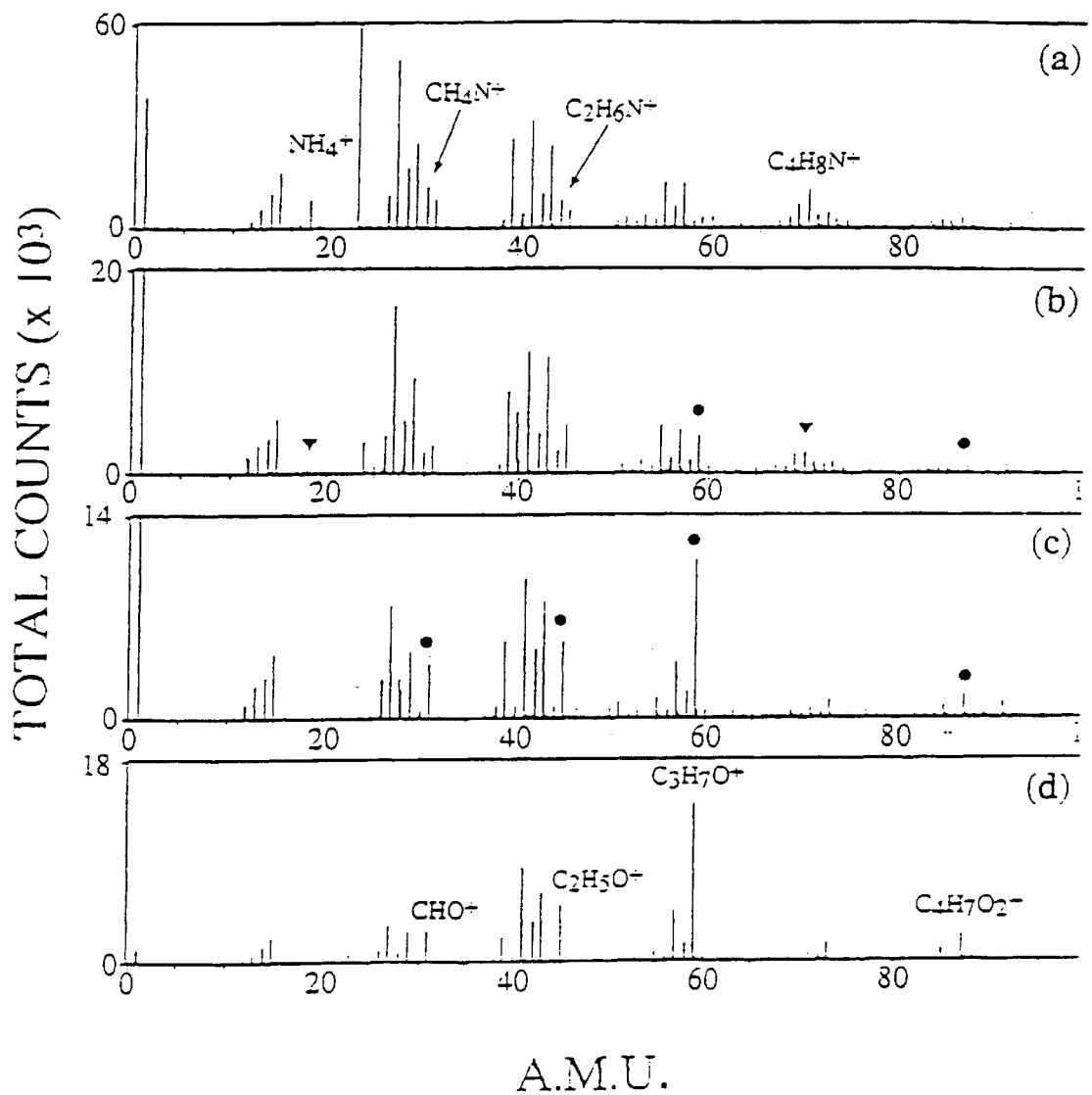
FIGS. 6a through 6d represent:
a) a positive fibronectin ToF SIMS reference spectrum;
b) a typical positive ToF SIMS spectrum recorded in conditioned hydrophilic area;
c) a typical positive ToF SIMS spectrum recorded in conditioned hydrophobic area;
d) a positive pluronic ToF SIMS reference spectrum.

In order to understand and to illustrate this segregation effect, ToF SIMS experiments (spectra and images) were performed. Positive and negative ToF SIMS spectra obtained on conditioned (with fibronectin as protein in this case) samples are presented in FIGS. 6 and 7 together with reference spectra of pluronic and fibronectin obtained by deposition from solutions on Si wafer. From the positive fibronectin reference spectrum (FIG. 6a), some protein characteristic peaks can be extracted. We selected mainly nitrogen containing peaks (like $NH_4^+$, $CH_4N^+$, $C_2H_6N^+$ and $C_4H_8N^+$) which are detected as even ions. For the positive pluronic spectrum (FIG. 6d), different peaks might be attributed to the different triblock copolymer constituents (PEO and PPO). As an example, the $C_3H_7O^+$ and $C_2H_5O^-$ are respectively attributed to the protonated PPO and PEO monomers [9]. In both cases, the $Si^+$ contribution was, if present, very small insuring no contribution from the substrate.

In order to compare the reference spectra with the spectra obtained in the hydrophilic (FIG. 6b) and hydrophobic (FIG. 6c) areas, the characteristic peaks of the protein and pluronic were followed. In the hydrophobic areas, no significant contributions from the proteins were detected. In fact, the spectrum was quite similar to the one obtained for pluronic except for the PS substrate contribution (77 and 91 a.m.u. peaks). This confirms the preferential surfactant adsorption in hydrophobic surfaces. In the hydrophilic tracks, the spectrum is more complex. Indeed, the spectrum is the sum of different contributions coming from plasma and washing treatments as well as from surface conditioning. However, protein characteristic peaks (like $C_4H_8N^+$ at 70 a.m.u.) have only been significantly detected on those tracks after conditioning (compare FIGS. 3a and 6a). This insures the presence of the protein. The surfactant is detected by the presence of peaks like at 59 a.m.u. peak (PPO monomer). Indeed, as this peak is very weak before conditioning (FIG. 3a) and in the reference spectrum of the protein (FIG. 6a), we can conclude to the presence of both components in those hydrophilic tracks.

Figure 7:
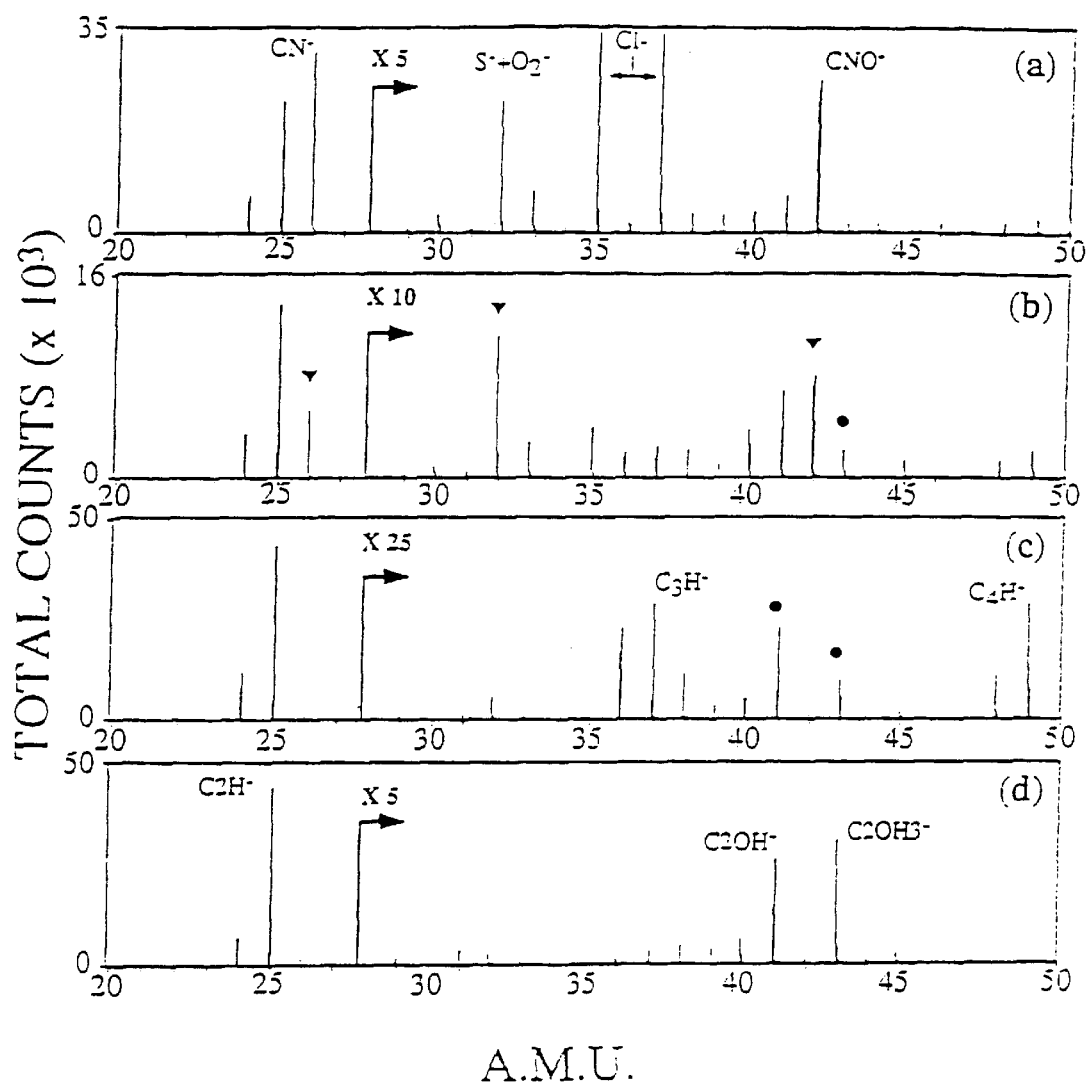
FIGS. 7a through 7d represent:
a) a negative fibronectin ToF SIMS reference spectrum;
b) a typical negative ToF SIMS spectrum recorded in conditioned hydrophilic area;
c) a typical negative ToF SIMS spectrum recorded in conditioned hydrophobic area;
d) a negative pluronic ToF SIMS reference spectrum.

In the negative spectra, the distinction between the different contributions is made easier owing to the smaller number of detected peaks. The negative spectra are presented in FIG. 7. The most characteristic peaks in the considered mass range are the $CN^-$, $S^-$ and $CNO^-$ for fibronectin (FIG. 7a), and $C_2OH^-$ and $C_2OH_3^-$ for pluronic (FIG. 7d). The negative SIMS results on the hydrophilic and hydrophobic areas confirms the conclusions drawn from the study of the positive spectra. In the hydrophobic areas (FIG. 7c), the spectrum is similar to the pluronic spectrum with additional hydrocarbon peaks from the PS substrate. In the hydrophilic tracks (FIG. 7b), both conditioning components were once again detected. The presence of pluronic revealed by the small contribution at 43 a.m.u. which was not detected before conditioning (FIG. 3d). Remark also that a large number of other peaks could have been used to draw the same conclusions.

Figure 8A:
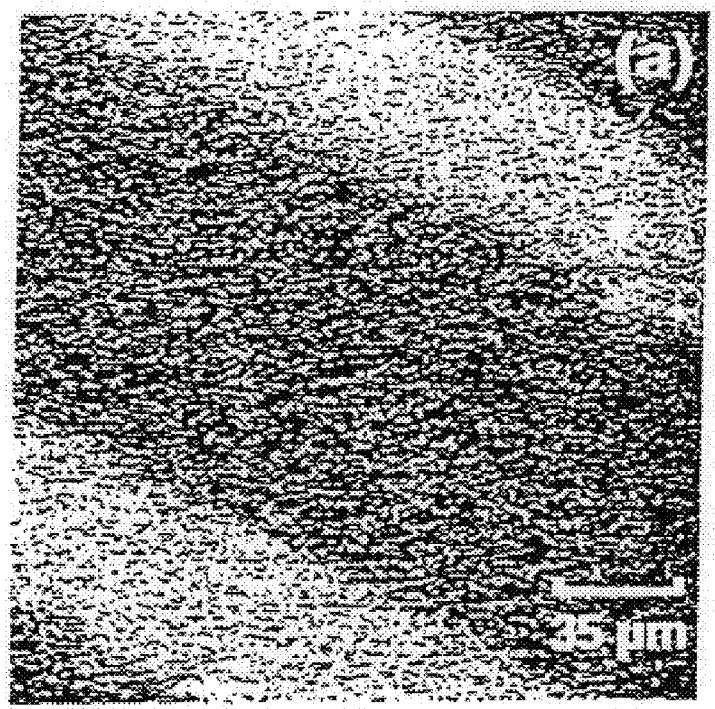
FIGS. 8a and 8b represent:
a) a ToF SIMS image recorded with $CNO^-$ ions on a conditioned heterogeneous surface;
b) a ToF SIMS image recorded with $NH^-$, $CN^-$, $S^-$ and $CNO^-$ ions on a conditioned heterogeneous surface.
Figure 8B:
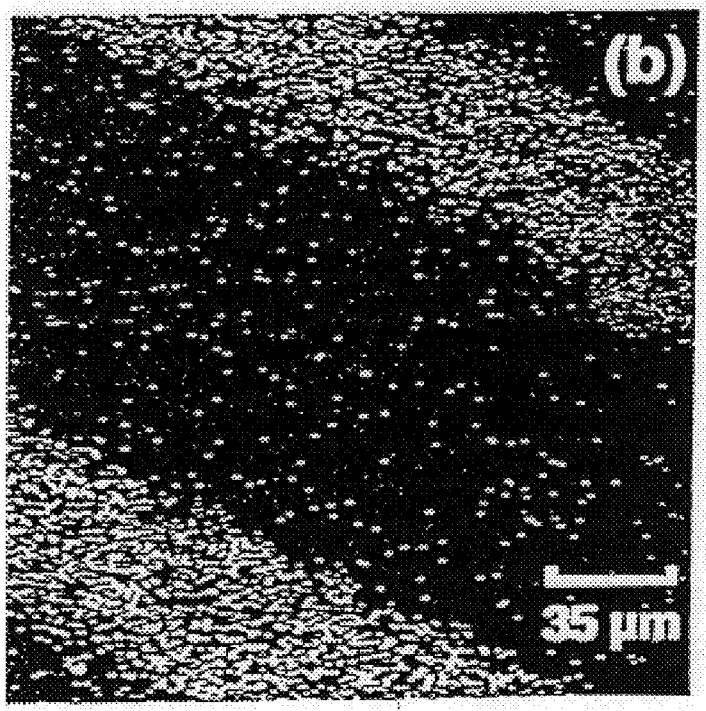

In order to illustrate the selective protein adsorption in the hydrophilic tracks, ToF SIMS images of the conditioned samples recorded with protein characteristic peaks are presented in FIGS. 8a and 8b. As it can be seen, the protein segregation is very strong. Even more, on FIG. 8a recorded with $CNO^-$ ions at 42 a.m.u., the very low intensity detected in the hydrophobic tracks might come from residual proteins but also from the background or $C_2H_2O^-$ contribution at 42.01 a.m.u. This last contribution was already detected in the hydrophobic areas before conditioning and might be due either to ethanol or even to the pluronic.

The characterization after conditioning revealed that for our samples, the hydrophobicity contrast between the different areas is large enough to induce a preferential surfactant adsorption in the more hydrophobic areas, leading to a protein selective adsorption in the more hydrophilic ones. As expected, the cells adhesion, spreading and proliferation occurred only where proteins were present. It is to be noticed that the other protein (collagen I) gave similar results.

If the cell adhesion results obtained for conditioned surfaces are well understood, it is not the case for the results obtained on the unconditioned surfaces when inoculated in serum containing medium. In that case, the cell segregation may be explained by preferential protein adsorption in the hydrophilic areas. But, when cells were inoculated in serum free culture medium, after conditioning with fibronectin alone, no contrast was revealed. This suggest that a molecule acting like a surfactant is present in the serum which could play the same rule than the pluronic. Its action is however not strong enough to induce an exclusive cell adhesion in the hydrophilic tracks.

TABLE 1

Surface composition as determined by XPS

| N° | Samples | C1s (%) | O1s (%) | N1s (%) | S2p (%) | Si2p (%) |
|---|---|---|---|---|---|---|
| L1 | Pristine PS | 98.7 | 1.3 | 0.1 | — | — |
| L2 | Resin and developer | 81.2 | 17.4 | — | 0.5 | 0.9 |
| L3 | PS Plasma treated | 75.2 | 23.9 | 0.9 | — | — |
| L4 | PS Plasma treated and washed | 84.1 | 15.3 | 0.5 | — | — |
| L5 | PS (developed resin) Plasma treated and washed | 82.1 | 17 | 0.8 | 0.1 | 0.1 |
| L6 | PS (undeveloped resin) Plasma treated and washed | 95.5 | 4.5 | — | — | — |

Note that only the average values are presented and that except for L2, at least two samples were analysed. The maximum deviations observed around those average values were less than 1% for C1s and O1s, and 0.2% for the other components.

TABLE 2

Contact angle measurements before and after plasma treatment.

| Samples | $\theta_a$ (°) | $\theta_r$ (°) |
|---|---|---|
| PS | 94 | 79 |
| PS (undeveloped resin) Plasma treated and washed | 90 | 59 |
| PS (developed resin) Plasma treated and washed | 58(1)*–65(2–3) | 10 |

*Figures under brackets stand for the corresponding cycles

EXAMPLE 2

Materials and Methods

1. Sample Preparation

Commercial polymethyl methacrylate (PMMA) (Oroglas V825 from Rohn & Haas, $M_w$=55700, $M_n$=44100) was spin casted on two different substrates from a solution (5% in weight) in dichloromethane ($CH_2Cl_2$) as solvent. By this method, uniform PMMA films a few µm thick were produced. For the ion beam degradation study, the substrate was a silicon wafer and for the cell culture tests, it was a Petri dish.

2. Ion Bombardment

Three different ion bombardment conditions were performed in separated systems:i) a $He^+$ beam from a Van de Graaf accelerator with 1 MeV energy, current of 12 nA and 3.4 mm² spot size, ii) a $Ga^+$ beam (FEE 83-2LI ion source) with 15 keV energy, 400 pA current, 0.1 µm spot size rastered on a 200 µm×200 µm surface area and iii) a $Xe^+$ beam (Kratos WG174 ion source) with 4 keV energy, 13.5 nA current, 300 µm spot size rastered on a 16 mm² surface area. The ion fluences were determined by integrating the current density measured by means of Faraday cups.

3. Cell Culture

The bombarded PMMA samples were first rinsed in a phosphate buffered saline solution (PBS). They were further reconditioned for one hour by immersion in a solution at physiologic pH (7.4) and osmolarity and containing both a protein (type I collagen; 33 µg/ml) and a non-ionic surfactant (Pluronic F68; 0.01% w/v). This surfactant is a triblock copolymer of poly(ethylene oxide) and poly(propylene oxide) ($PEO_{70}$-$PPO_{30}$-$PEO_{70}$). After reconditioning, the samples were then inoculated with human hepatoblastoma cells from the HepG2 line (ATCC HTB 8065) in a serum free nutritive medium. The cell density was in the order of 70,000 cells/cm². After a 24 hours incubation time at 37° C., the supernatant was removed and the samples were rinsed cautiously prior to fixation and coloration.

Figure 9:
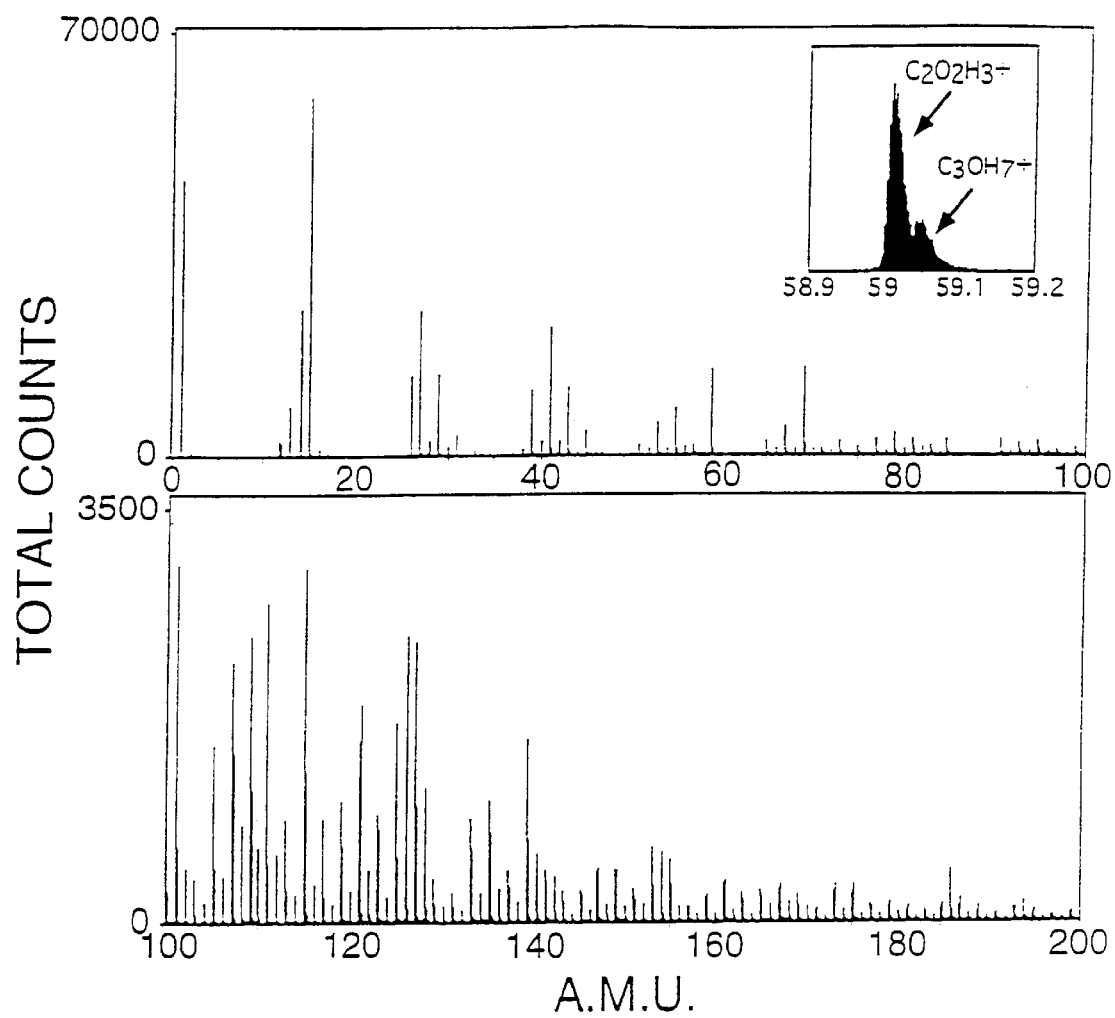
FIG. 9 represents the typical positive ToF SIMS spectrum of polymethyl methacrylate (PMMA).

FIG. 9 presents a typical positive ToF SIMS spectrum obtained on pristine PMMA. Most of the peaks originate from the hydrocarbon polymer backbone. The contribution from the methacrylate pendent group arises mainly at masses 59 and 69 amu [9]. The 59 amu peak contains two contributions which are resolved thanks to the high mass resolution of the ToF spectrometer. The most intense corresponds to $C_2O_2H_3^+$ ($O=C^+-O-CH_3$) and the weaker, to $C_3OH_7^+$. The 69 amu peak contains three contributions $Ga^+$, $C_4OH_5^+$ and $C_5H_9^+$. On bombarded samples, hydrocarbon peaks at 77 and 91 amu are seen to increase initially. They correspond to aromatic ions respectively $C_6H_5^+$ and $C_7H_7^+$. Their detection indicates presence of aromaticity and/or unsaturation [11]. The ion beam degradation of PMMA can be studied by looking at the fluence dependence of those four peak intensities.

Figure 10:
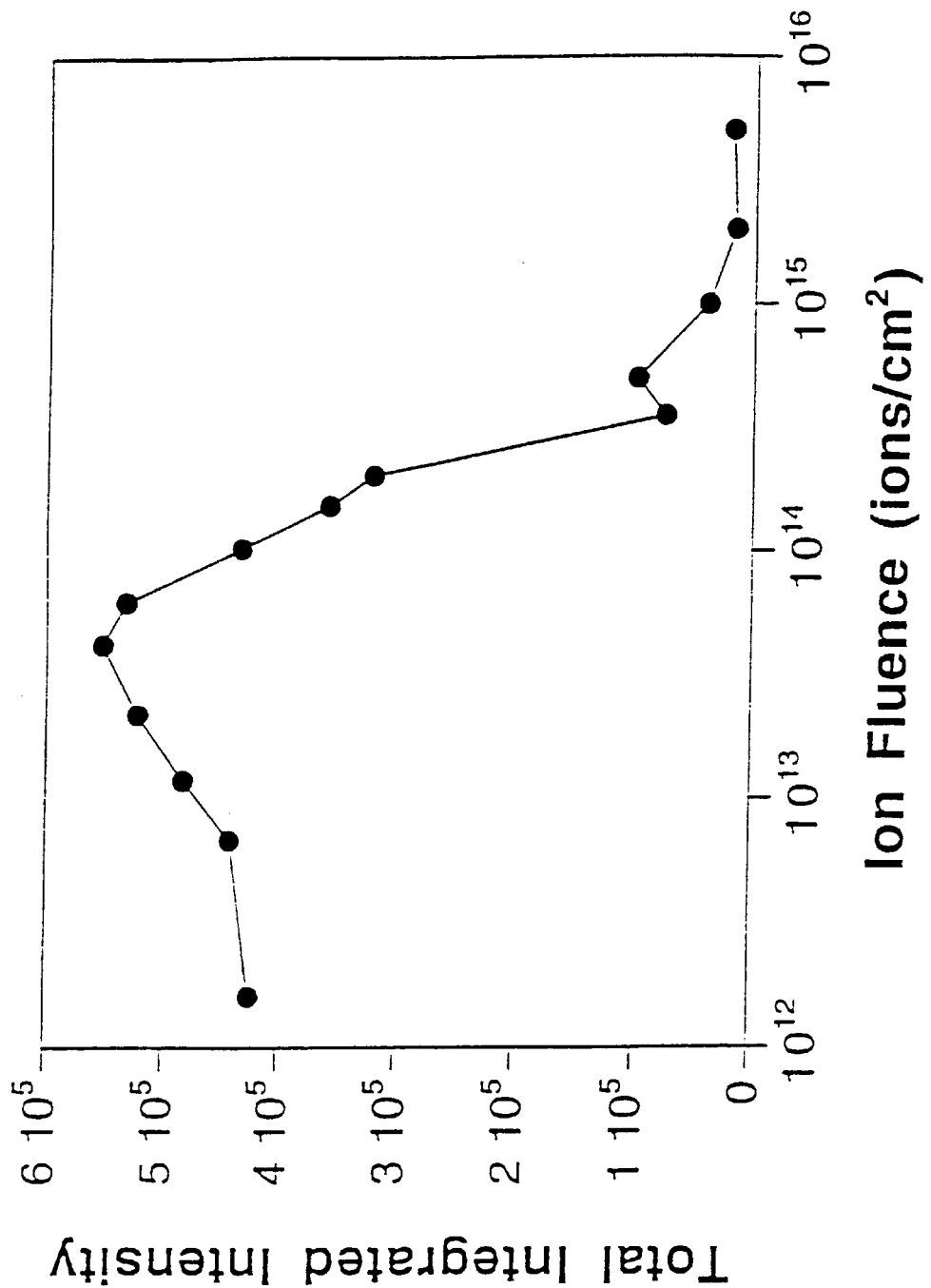
FIG. 10 represents the evolution of total integrated intensity as a function of the incidence ion fluence.

The results for $Ga^+$ (15 keV) bombardment are first presented. They were obtained and analyzed "in situ" in the ToF-SIMS spectrometer. FIG. 10 shows the variation of the integrated SIMS intensity as a function of the prebombardment ion fluence. This total integrated intensity is obtained by summing all the peak intensities in the spectrum but with the exception of the $H^+$ and $Ga^+$ intensities. Indeed the $H^+$ intensity is barely reproducible and for $Ga^+$, its intensity becomes predominant for ion fluences >$10^{15}$ $Ga^+/cm^2$ due to its implantation and its higher ionic yield. The integrated intensity increases slowly up to a maximum (at 4 $10^{13}$ $Ga^+/cm^2$) then decreases sharply for higher fluences. The initial increase is related to the chain fragmentation which favours the secondary molecular ion emission. The rapid intensity drop is related to the formation of a highly crosslinked more and more unsaturated hydrocarbon network leading to an overall secondary ion yield decrease. A stabilization seems to be reached for fluences higher than $10^{15}$ $Ga^+/cm^2$.

Figure 11:
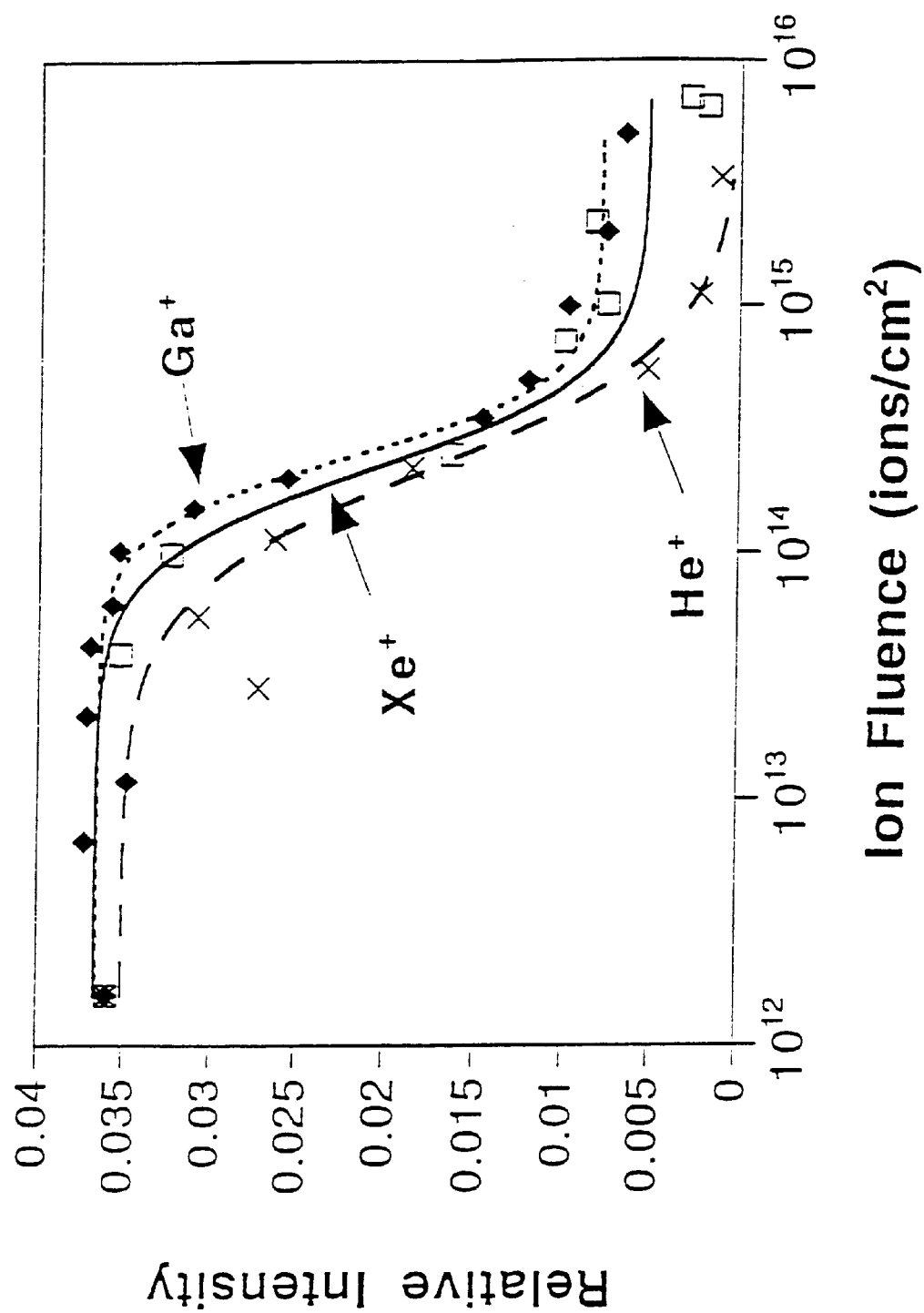
FIG. 11 represents the evolution of the relative intensity of the peak at 59 a.m.u. as a function of the incident ion fluence (lozenges for $Ga^+$ bombardment, squares for $Xe^+$ and crosses for $He^+$).

A more detailed view of the degradation is obtained by looking at the fluence evolution of the peaks characteristic of the pendent group (59 and 69 amu) and of the unsaturation (77 and 91 amu). The dependence of the 59 amu relative intensity (peak intensity divided by total integrated intensity) on the ion fluence is shown in FIG. 11. For ion fluences lower than $10^{14}$ $Ga^+/cm^2$, the 59 amu relative intensity stays nearly constant then it decreases for higher fluences. This decrease can be characterized by the crtical fluence F* measured at half maximum (F*=2.8 $10^{14}$ $Ga^-/cm^2$) and can be related to the already proposed PMMA fragmentation mechanism. In this mechanism, the loss of the pendent group is associated to the PMMA main chain cleavage [10]. Although this mechanism can not explain alone all the observed contributions in the SIMS spectra of PMMA, it explains however the most intense peaks detected below 100 amu [12]. The other oxygenated secondary ions present a similar decrease and this oxygen loss under irradiation was also observed by XPS (see below and ref. [10]).

Figure 12:
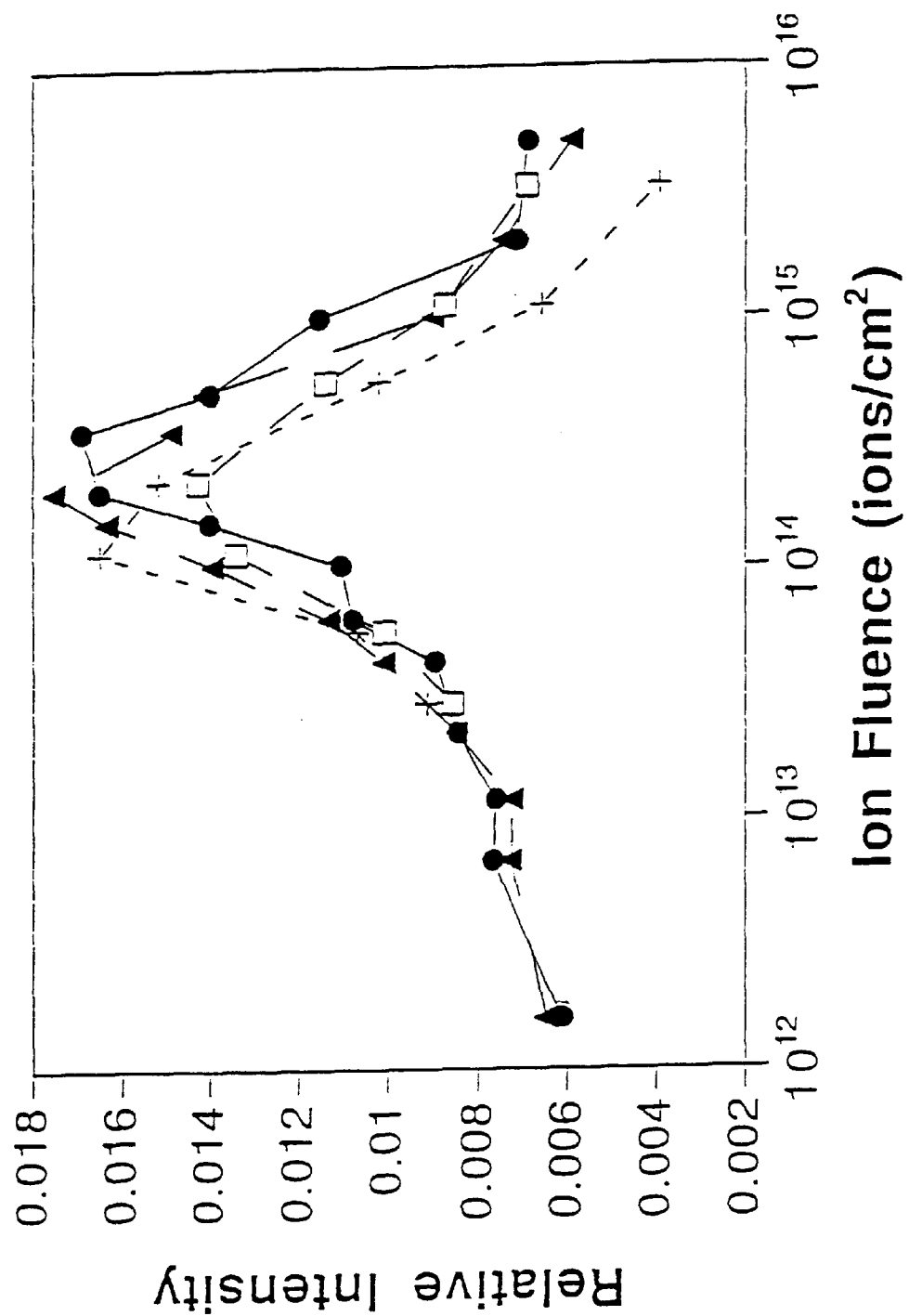
FIG. 12 represents the evolution of the relative intensity of the peak at 77 and 91 a.m.u. as a function of the incident ion fluence (77 a.m.u. peak:squares for $He^+$ bombardment and circles for $Ga^+$; 91 a.m.u. peak:crosses for $He^+$ bombardment and triangles for $Ga^+$).

The 77 and 91 amu relative intensities are presented as a function of the ion fluence in FIG. 12. A sharp maximum is observed for nearly the same critical fluence F*. The first increase is due to the production of unsaturation while the decrease, to the formation of the unsaturated, crosslinked surface network (see supra). It has been suggested that crosslinking causes a decrease the total integrated intensity [13]. This was indeed observed in FIG. 9. Moreover, we found that ion beam irradiation modifies also the relative intensities of the different carbon clusters in the SIMS spectra leading to an increase of the clusters with a smaller carbon content. The relative intensities of the $C_iH_j^+$ ions were found to increase continuously with the fluence even above F* for i=1, 2. This has to be related to the formation of the unsaturated crosslinked network. Surface dehydrogenation is also evidenced from the observed intensity shift in the different C clusters towards ions with a lower content of H [17].

Figure 13:
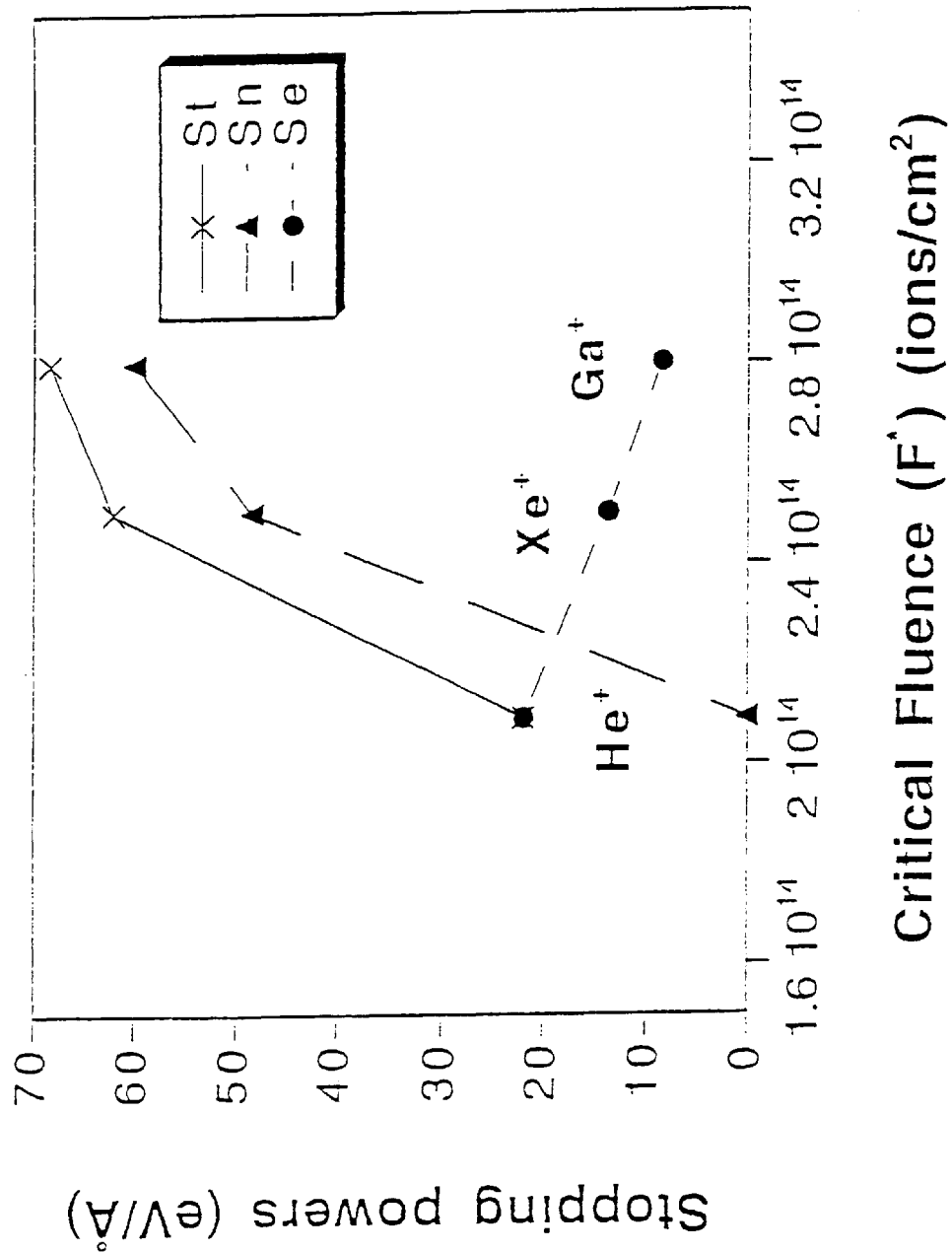
FIG. 13 represents stopping powers as a function of the critical ion fluence (F*).

PMMA surfaces were also analyzed by TOF-SIMS after $He^+$ (1 MeV) and $Xe^+$ (4 keV) bombardment. The results are compared with the $Ga^+$ (15 keV) results in FIGS. 11 and 12. Similar fluence dependencies are observed. The corresponding critical fluences F* (2.1 $10^{14}$ $He^+/cm^2$ and 2.5 $10^{14}$ $Xe^+/cm^2$) are however lower indicating in both cases an increased degradation. In order to interpret these results the critical fluences F* are presented in FIG. 13 as a function of the stopping powers $S_i$ (nuclear, electronic and total). The stopping powers $S_n$, $S_e$ and $S_t$ were calculated by means of a TRIM (Transports of Ions in Matter) program [15] and their values are shown in Table 3. From FIG. 5, it is clear that $S_n$ can not be responsible for the observed variation of F*. Indeed their variations are in opposition, a higher degradation (decrease of F*) is seen for lower values of $S_n$. The decrease of F* is however well correlated with the increase of $S_e$. The product F*$S_e$ gives a characteristic energy density deposited in the polymer by electronic excitation; this is of the order of 0.2–0.5 $eV/Å^3$. It can be concluded that the most important contribution to the PMMA degradation is the electronic stopping power.

Figure 14A:
FIGS. 14a and 14b represent the adhesion of HepG2 cells on reconditioned PMMA samples after ion beam bombardment. After 24 hours inoculation time in a serum free medium, cells (black spots) adhere and colonize only the bombarded area.
Figure 14:
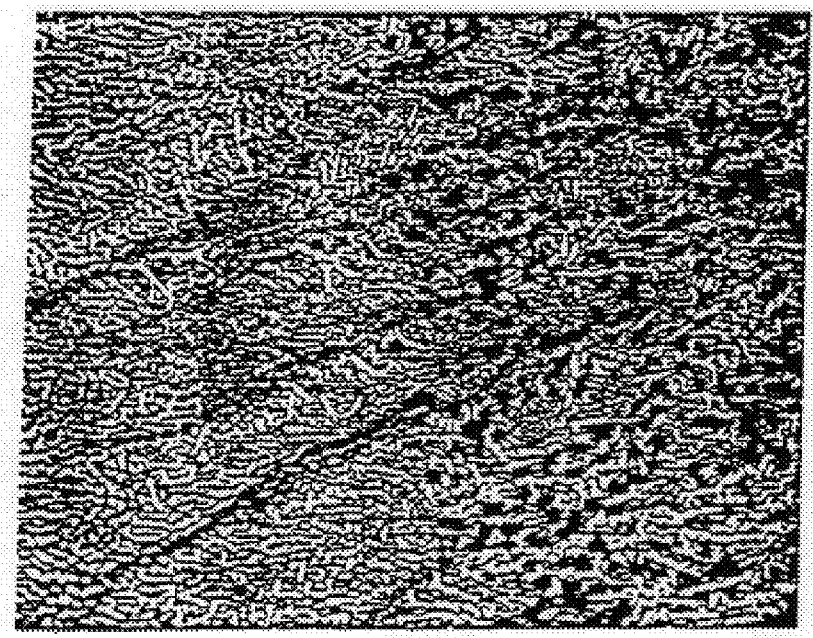

In order to evaluate the influence of the ion beam treatments on cell adhesion, cell inoculations were performed. As previously mentioned, the substrates were reconditioned before cell inoculation with a solution containing both a protein and a surfactant. Their mutual influence will depend on the surface areas where they will adsorb. It has been shown that the surfactant adsorbs irreversibly on more hydrophobic regions while the protein will adsorb on more hydrophilic ones when both are in competition [1, 16, 17]. Optical microscopy photos of the samples after cell inoculation are presented in FIG. 14a) for the sample bombarded with 4 $10^{14}$ $He^+/cm^2$ and in FIG. 14b), with 5 $10^{15}$ $Xe^+/cm^2$. These fluences were higher than F*. It can been seen that the cells (black spots) adhere only on the bombarded areas. The spectacular effect of ion bombardment on cell adhesion is believed to be produced by a preferential protein adsorption on the bombarded areas and surfactant adsorption on the untreated ones. The interpretation of this effect is however not trivial because it seems to be contradictory. Indeed one of the effect of the ion beam has been shown to be the removal of the surface oxygen functionalities which are known to contribute to the hydrophilic character of the surface. XPS results obtained on the bombarded regions confirmed the oxygen depletion (see on Table 4). Nevertheless cell adsorption is only observed on bombarded areas. The more hydrophilic character of the bombarded areas were however observed by rinsing the samples in a PBS solution. The liquid was shown to wet only the bombarded regions.

ToF-SIMS results allowed to follow the surface modification of PMMA under ion bombardment. The main observed effects are the loss of the pendent group, production of unsaturation and cross linking. A critical fluence for degradation can be associated to the different bombardment conditions and it is shown that it depends mainly on the electronic stopping power. The ion bombardment has a spectacular effect on cell adhesion provided that a characteristic energy density is deposited by the beam in electronic excitations and that the bombarded surface is reconditioned in a adequate medium before cell inoculation.

TABLE 3

| | Stopping powers (from TRIM) | | |
|---|---|---|---|
| | $S_e$ (eV/Å) | $S_n$ (eV/Å) | $S_t$ (eV/Å) |
| $He^+$ (1 MeV) | 21.9 | 0.025 | 21.9 |
| $Ga^+$ (15 keV) | 8.4 | 60 | 68.4 |
| $Xe^+$ (4 keV) | 13.7 | 48.4 | 62.1 |

TABLE 4

XPS quantitative analyses of ion bombarded PMMA surfaces

| | C1s % | O1s % |
|---|---|---|
| 5 $10^{15}$ $Xe^+$ (4 keV)/$cm^2$ | 85.9 | 14.2 |
| 4 $10^{14}$ $He^+$ (1 MeV)/$cm^2$ | 81.8 | 18.3 |
| Pristine surface | 72.4 | 27.6 |
| Stoichiometry values | 71.4 | 28.6 |

EXAMPLE 3

The solid support according to the invention was obtained as described in the example 1.

The cells were inoculated in the wells of a polystyrene microplate (24 wells) obtained from Falcon and comprising the biomaterial according to the invention.

Cells

Schwann cells from MSC80 mouse in DMEM medium containing glutamine 4 mM (obtained from Bio Whittaker) and added with 10% of foetal calf serum (obtained from PAA Labor) and 1% antibiotic (penicillin 10000 U/ml and streptomycin 10000 cgm/ml obtained from Bio Whittaker). The inoculation density is 100000 cells/well;

hepatocytes obtained from primary culture in William's E medium (obtained from Sigma) added with 10% of foetal calf serum (obtained from PAA Labor) and 1% antibiotic (penicillin 10000 U/ml and streptomycin 10000 cgm/ml obtained from Bio Whittaker). The inoculation density is 250000 cells/well.

After 4 hours of culture in the seric medium, the hepatocytes cultures were added with PBS and the medium was replaced by the hormono defined medium hereafter described:

William's E medium (obtained from Gibco) added with 1% antibiotic (penicillin 10000 U/ml and streptomycin 10000 cgm/ml obtained from Bio Whittaker), added with dexamethasone (obtained from Sigma) 0,1 mM, EGF (obtained from Gibco BRL) 50 ng/ml, ascorbic acid (obtained from Sigma) 0,1 mM, insulin (obtained from Novo Nordisk) 10 ng/ml, and linoleic acid complexed with BSA (obtained from Sigma) 10 μg/ml.

After inoculation, the cells are cultivated in an incubator at 37° C. saturated in water and containing an atmosphere with 5% $CO_2$. FIGS. 15 and 16 show the MSC80 cell (FIG. 15) and hepatocytes (FIG. 16) obtained after 48 hours.

REFERENCES

[1] J.-L. Dewez, Y.-J. Schneider and P. Rouxhet, *J. Biomed. Mater. Res.* submitted.

[2] J. Helbert in: *Handbook of VLSI Microlithography*, chap. 2, W. B. Glendinning and J. Helbert (Ed.). Noyes Publications, Park Ridge, N.J., U.S.A. (1991).

[3] L. A. Greene and A. S. Tischler, *Procédé. Natl. Acad. Sci. USA* 73, 2424 (1976).

[4] F. M. Petrat, D. Wolany, B. C. Schwede, L. Wiedmann and A. Benninghoven, *Surf. Interface Anal.* 21, 402 (1994).

[5] F. M. Petrat, D. Wolany, B. C. Schwede, L. Wiedmann and A. Benninghoven in: *Secondary Ion Mass Spectrometry SIMS IX*, p. 760, A. Benninghoven, Y. Nihei, R. Shimizu and H. W. Werner (Ed.). John Wiley & Sons, Chichester, Great-Britain (1994).

[6] R. Foerch and D. Johnson, *Surf. Interface Anal.* 17, 847 (1991).

[7] J.-B. Lhoest, J.-L. Dewez and P. Bertrand, *Nucl. Instr. and Meth. B* accepted for publication.

[8] J. G. Steele, B. A. Dalton, G. Johnson and P. A. Underwood, *J. Biomed. Mater. Res.* 27, 927 (1993).

[9] D. Briggs, A. Brown and J. C. Vickerman in: *Handbook of Static Secondary Ion Mass Spectrometry* (SIMS); J. Wiley & Sons (Ed.). Chichester, Great-Britain (1989).

[10] D. Briggs and M. J. hearn, *Vacuum* 36, 1005 (1986).

[11] W. J. van Ooij and R. H. Brinkhuis, *Surf. Interf. Anal.* 11, 430 (1988).

[12] P. A. Zimmerman and D. M. Hercules, *Anal. Chem.* 65, 983 (1993).

[13] A. Chilkoti, G. P. Lopez, B. D. Ratner, M. J. Hearn and D. Briggs, *Macromolecules* 26, 4825 (1993).

[14] A. Delcorte, L. T. Weng and P. Bertrand, to be published in *Nucl. Instrum. Meth. Phys. Revêtements. B*.

[15] J. F. Ziegler, J. P. Biersack and U. Littmark, *The Stopping and Range of Ions in Solids* (Pergammon, N.Y.) (1985).

[16] S. Wellin-Klinström, A. Askendal and H. Elwing, *J. Colloid Interf. Sci.* 158, 188 (1993).

[17] L. M. A. van de Steeg and C.-G. Gölander, *Colloids Surfaces* 55, 105 (1991).

We claim:

1. A method for obtaining a biomaterial for selective adhesion of cells and/or tissues said method, comprising the steps of: forming heterogeneous surface areas on a polymeric support by partial surface modification to create modified and non-modified areas on the surface of the polymeric support; and treating the polymeric support with a surfactant and a protein of an extracellular matrix or a portion thereof such that said protein or portion thereof preferentially binds to said modified area.

2. A method according to claim 1, wherein an ion beam is used to form said heterogeneous surface area on the polymeric support.

3. A method according to claim 1, wherein the ion beam has a fluence between $10^{10}$ and $10^{20}$ ions/cm² of the polymeric support surface.

4. A method for obtaining a biomaterial according to claim 1, comprising the steps of: forming heterogeneous surface areas on a polymeric support by covering the polymeric support with a patterned mask, exerting a plasma discharge over the patterned mask, and removing the mask, to create modified and nonmodified areas on the surface of the polymeric support; and treating the polymeric support with a surfactant and a protein of the extracellular matrix or a portion thereof.

5. A method according to claim 4, wherein the surface of the polymeric support is treated with a plasma $O_2$ discharge.

6. A method according to claim 4, wherein the surface of the polymeric support is treated for between 10 sec and 60 sec with a plasma discharge at around 50 Watts.

7. A method according to claim 3, wherein the fluence of the ion beam is between $10^{12}$ and $10^{16}$ ions/cm² of the polymeric support surface.

8. A cell- or tissue-patterned biomaterial, comprising a biomaterial having, conditioned heterogeneous surface areas produced according to the method of claim 1, and cells or tissues inoculated and grown on the biomaterial in accordance with the treated heterogeneous surface areas.

9. A biomaterial produced according to the method of claim 1, wherein the binding characteristics of the heterogeneous surface areas differ in hydrophobicity.

10. A biomaterial produced according to the method of claim 1, wherein the partial surface modification is achieved by an ion beam treatment of the surface areas to be modified.

11. A biomaterial produced according to the method of claim 1, wherein the partial surface modification is achieved by a plasma discharge treatment of the surface areas to be modified.

12. A biomaterial produced according to the method of claim 1, wherein the polymeric support is selected from the group consisting of olefin polymers, fluorin polymers, polystyrene, polyacrylic polymers, polyester polymers, polyurethane polymers, silicon polymers, cellulose polymers, epoxy polymers, and a mixture of the foregoing.

13. A biomaterial produced according to the method of claim 1, wherein the polymeric support consists of one or more elements selected from the group consisting of carbon, hydrogen, oxygen, and nitrogen.

14. A biomaterial produced according to the method of claim 1, wherein the surfactant is selected from the group consisting of fatty acids, fatty acid esters, fatty acid amides, proteins, saccharides, lipids, non-ionic surfactants, and a mixture of the foregoing.

15. A biomaterial produced according to the method of claim 1, wherein the surfactant is a non-ionic surfactant.

16. A biomaterial according to claim 15, wherein the non-ionic surfactant is a triblock copolymer.

17. A biomaterial according to claim 16, wherein the triblock copolymer is made of polyethylene oxide-polypropylene oxide-polyethylene oxide.

18. A biomaterial according to claim 14, wherein the surfactant is albumin.

19. A biomaterial produced according to the method of claim 1, wherein the extracellular matrix protein is selected from the group consisting of collagen, laminin, fibronectin, fibrin, chondronectin, and a mixture of the foregoing.

20. A biomaterial according to claim 17 wherein the triblock copolymer is polyethylene oxide-polypropylene oxide-polyethylene oxide.

21. A biomaterial according to claim 20 wherein the polyethylene oxide-polypropylene oxide-polyethylene oxide is $PEO_{70}$-$PPO_{30}$-$PEO_{70}$.

22. A method according to claim 1, wherein the ion beam is selected from the group consisting of a $He^+$ beam, a $Xe^+$ beam and a $Ga^+$ beam.

* * * * *